United States Patent [19]

Ahnell

[11] 4,152,213

[45] May 1, 1979

[54] VACUUM DETECTION OF BACTERIA

[75] Inventor: Joseph E. Ahnell, Hydes, Md.

[73] Assignee: Johnston Laboratories, Inc., Cockeysville, Md.

[21] Appl. No.: 776,426

[22] Filed: Mar. 10, 1977

[51] Int. Cl.$^2$ .................................................. C12K 1/04

[52] U.S. Cl. ...................... 195/103.5 M; 195/103.5 P; 195/127

[58] Field of Search .................. 195/103.5 M, 103.5 P

[56] References Cited

U.S. PATENT DOCUMENTS 3,907,646 9/1975 Wilkins et al. ............... 195/103.5 M

*Primary Examiner*—Raymond N. Jones
*Assistant Examiner*—Robert J. Warden

[57] ABSTRACT

A sample of material to be tested for the presence of oxygen consuming bacteria is introduced into a sealable container partially filled with a culture medium; the remainder of the container being filled with an oxygen containing gas, the container being connected to means for sensing the production of a vacuum therein. The container and its contents are subjected to conditions conducive to bacterial growth for a predetermined period sufficient for growth of bacteria to consume some of the oxygen, during which time the pressure of the gas in the container is monitored and compared to the initial pressure in order to detect the production of a vacuum due to consumption of oxygen by bacteria from the test sample, thereby indicating the presence or absence of oxygen consuming bacteria in the sample of test material.

35 Claims, 11 Drawing Figures

VACUUM RESPONSE VS. INCUBATION TIME FOR THE ORGANISM
P. PSEUDOALCALIGENES

VACUUM RESPONSE VS. INCUBATION TIME FOR THE ORGANISM S. BOVIS

VACUUM RESPONSE VS. INCUBATION TIME FOR THE ORGANISM P. AERUGINOSA

VACUUM RESPONSE VS. INCUBATION TIME FOR THE ORGANISM E. CLOACAE

VACUUM RESPONSE VS. INCUBATION TIME FOR THE ORGANISM E. COLI

VACUUM RESPONSE VS. INCUBATION TIME FOR THE ORGANISM S. AUREUS

VACUUM RESPONSE VS. INCUBATION TIME FOR THE ORGANISM P. MIRABILIS

VACUUM RESPONSE AS A FUNCTION OF RELATIVE INITIAL INOCULUM, E. COLI

INCUBATION TIME AS A FUNCTION OF INITIAL INOCULUM REQUIRED TO:

○ – OBTAIN VACUUM DETECTION
△ – REACH MAXIMUM VACUUM
□ – REGAIN ZERO PRESSURE
× – UNKNOWN SAMPLE

VACUUM RESPONSE AS A FUNCTION OF RELATIVE INITIAL INOCULUM P. AERUGINOSA

VACUUM DETECTION OF BACTERIA

BACKGROUND OF THE INVENTION

In many fields of endeavor it is important to be able to determine whether or not materials are contaminated with bacteria or the like. Examples of such fields are the medical field, the food processing industry, the pharmaceutical industry, the cosmetics industry, the field of public health, and interplanetary space exploration.

In the past, it has been a standard practice to place a sample of a material to be tested for the presence of bacteria in an appropriate growth medium or a Petri dish and to make visual observations of the resulting microbial growth, if any. Not only are such culturing methods slow and laborious, but because they depend on the subjective judgment of individual human observers, the result obtained is not uniformly reliable.

Techniques have also been developed for detection of bacteria which involve incubating a sample of material to be tested in a closed container with a radioactive isotope labeled culture medium and monitoring the atmosphere in the container above the medium to determine whether or not radioactive gases are produced. A radiometric system of this type is disclosed in U.S. Pat. Nos. 3,676,679 and No. 3,935,073. Radiometric systems are rapid and reliable, but they suffer from a number of disadvantages. In the first place, radioactively labeled materials are not inexpensive and require special handling during storage, use and disposal. Moreover, although the levels of radioactivity encountered in using such systems are very low, prospective users may be deterred by personal fears of radioactivity. The use of radioactive isotopes in instrumental systems has generally been resorted to in order to facilitate detection of minute quantities of metabolic product gases thereby to detect rapidly the presence of bacteria.

Wilkins, U.S. Pat. No. 3,907,646, discloses a method for bacteria detection and quantification based on measurement of an increase in the pressure of the culture gas above a liquid culture medium in a sealed vial. Although this method is simple, it appears to be relatively insensitive and does not give faster detection than is achieved by visual observation of the turbidity of the medium.

It has long been known that many bacteria consume oxygen, but it has been thought that no vacuum would be produced because the oxygen was replaced by evolved carbon dioxide. The comment of Arthur is typical:

"In a closed system, as bacteria utilize oxygen and create carbon dioxide, there is no effective change in pressure." (U.S. Pat. No. 3,740,320, Col. 3, 11. 28–29) Thus where it has been attempted to measure the consumption of oxygen by known microorganisms, either with a Warburg Apparatus or in some other complex system, a carbon dioxide absorber has invariably been included in the system to capture all evolved carbon dioxide thereby to prevent the evolved carbon dioxide from obliterating the oxygen consumption; see Poepel, U.S. Pat. No. 3,282,803; Arthur, U.S. Pat. No. 3,740,320 and Umbreit, *Manometric and Biochemical Techniques*, Burgess Publishing Company, Minneapolis, 1972.

In the introduction to his patent on radiometric petroleum prospecting, U.S. Pat. No. 2,777,799, Davis cursorily mentions attempts at petroleum prospecting by incubating soil samples in an atmosphere containing gaseous hydrocarbon and measuring the decrease of the pressure of the atmosphere due to consumption of the hydrocarbon by hydrocarbon consuming bacteria found in earth formations near petroleum deposits. Such attempts are described as unsatisfactory because pressure decreases occur for reasons other than consumption of hydrocarbon by the desired bacteria, and Davis teaches instead a radiometric assay technique.

Attempts to avoid radiometric techniques for bacterial detection have often been complicated, unwieldy and cumbersome like the indirect measurement of oxygen production from $H_2O_2$ by the enzyme catalase disclosed in Groves, U.S. Pat. No. 3,838,034.

There is a requirement, especially in medical and industrial applications, for a simple and very rapid non-radioactive method for the detection and quantification of the microorganisms in a test sample. Speed is of the essence since faster detection, at least in the medical field, allows faster application of appropriate treatment. Simplicity, reliability and low cost are also of paramount importance. These advantages may best be obtained in automated instrumental systems. Thus, there exists a need for a rapid, non-radioactive instrumental system for detecting bacteria.

Accordingly, it is an object of the present invention to provide a rapid method for detecting the presence or absence of bacteria.

Another object of the invention is to provide a method for rapidly detecting the presence or absence of bacteria which uses comparatively inexpensive materials.

It is a further object of the present invention to provide an instrumental method for detecting the presence or absence of bacteria which is not subject to the vagaries of subjective human observations.

Another object of the present invention is to provide an instrumental system for detecting the presence or absence of bacteria which avoids the use of radioactive materials.

Another object is a method for rapid detection of microorganisms using a method that is simple, easy to use and can handle a plurality of samples.

A further object of the present invention is to provide an instrumental method for measuring microorganism growth that can be scanned automatically and electronically to detect such growth.

It is likewise an object of this invention to provide a method for detecting bacteria by measuring vacuum production by microorganisms when grown in a culture medium in a sealed vial.

An additional object of the invention is to provide a method of quantifying the number of oxygen consuming microorganisms in a test sample.

Further objects of the invention will be apparent from a consideration of the following description.

SUMMARY OF THE INVENTION

These and other objects of the invention are achieved by providing a method for detecting the presence of oxygen consuming bacteria comprising the steps of providing a sealable, sterile container free of $CO_2$ absorbers containing a sterile, non-radioactive, liquid culture medium and a quantity of substantially hydrocarbon free, oxygen containing gas above the culture medium; inoculating the container with a sample of material to be tested for the presence of oxygen consuming bacteria and sealing the container; the container being connected to means for sensing the production of a vacuum therein; subjecting the sealed, inoculated container and its contents to conditions conducive to bacterial growth for a period of time sufficient for growth of bacteria to consume some of the oxygen; retaining in the gas any gases evolved from the culture medium into the gas and monitoring the container for the production of a vacuum due to consumption of oxygen by bacteria growing in the liquid culture medium.

The present invention also comprises a method for determining the number of oxygen consuming bacteria present in a sample of material comprising the steps of providing a sealable, sterile container containing a sterile, non-radioactive, liquid culture medium and a quantity of substantially hydrocarbon free, oxygen containing gas above said culture medium; inoculating the container with a sample of material in which the number of oxygen consuming bacteria is to be determined and sealing the container; said container being connected to means for sensing the production of a vacuum therein; subjecting the sealed inoculated container and its contents to conditions conducive to bacterial growth for a period of time sufficient for growth of bacteria to consume some of the oxygen; retaining in the gas any gases evolved from the culture medium into the gas; monitoring the pattern of vacuum production in said container with respect to time due to consumption of oxygen by bacteria growing in the liquid culture medium, and comparing the monitored pattern of vacuum production with the pattern of vacuum production for samples of material containing known numbers of the same bacteria treated in the same manner.

DETAILED DESCRIPTION OF THE PREFERRED EMBODIMENTS

Figure 1:
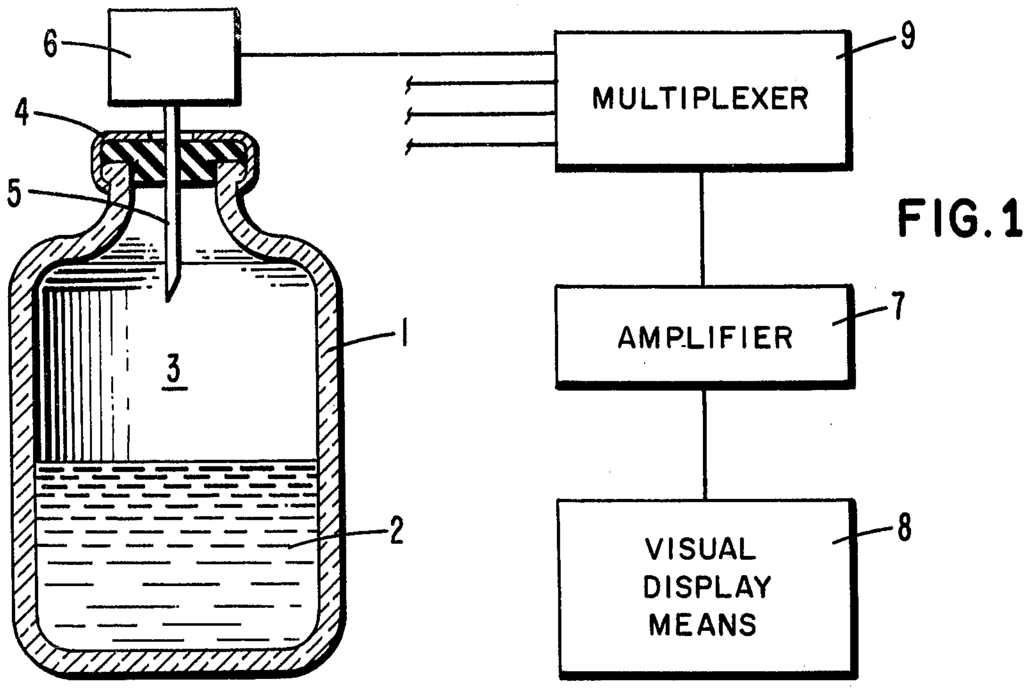
FIG. 1 is a schematic representation of apparatus utilized in practicing the method of the invention.

Turning now to FIG. 1, reference numeral 1 designates a culture via utilized in the practice of the method of the present invention. Vial 1 is partially filled with a culture medium 2. Typical culture media generally contain water, a carbon source, a nitrogen source, calcium, magnesium, potassium, phosphate, sulfate, and trace amounts of other minor elements. The carbon source may be a carbohydrate, amino acid, mono- or dicarboxylic acid or salt thereof, polyhydroxy alcohol, hydroxy acid or other metabolizable carbon compound or mixture. Usually the carbon source will comprise at least one sugar such as glucose, sucrose, fructose, xylose, maltose, lactose, etc. Amino acids such as lysine, glycine, alanine, tyrosine, threonine, histidine, leucine, etc. also frequently comprise part of the culture media carbon source.

The nitrogen source may be nitrate, nitrite, ammonia, urea or any other assimilable organic or inorganic nitrogen source. An amino acid might serve as both a carbon and a nitrogen source. Sufficient nitrogen should be present to facilitate cell growth.

A variety of calcium, potassium and magnesium salts may be employed in the culture medium including chlorides, sulfates, phosphates and the like. Similarly, phosphate and sulfate ions can be supplied as a variety of salts. As such materials are conventional in fermentation media, the selection of specific materials as well as their proportions is thought to be within the skill of the art.

The so called minor elements which are present in trace amounts are commonly understood to include manganese, iron, zinc, cobalt and possibly others.

Due to the fact that most bacteria do not grow well in strongly acidic or strongly alkaline media, suitable buffers such as potassium or ammonium phosphates may be employed, if desired, to maintain the pH of the culture medium near neutral. The pH ordinarily is buffered to a value between about 6 and 8. Of course the effect of culture medium pH varies from microorganism to microorganism. Tests conducted with the organism *Proteus mirabilis* show that vacuum production is strongly retarded at a pH of 6.25, slightly retarded at pH 7.04 and occurs comparatively rapidly at pH 7.90 while tests conducted with *Escherichia coli* show retarded vacuum production at pH 6.25, more rapid vacuum production at pH 7.04 and essentially no vacuum production at pH 7.90. Preferably, the pH will be buffered to between 6.9 and 7.4 since most microorganisms show good vacuum production in that range.

Examples of well known culture media which may be used in the present invention are those created by papaic or pancreatic digestion of suitable protein such as gelatin, soy meal, animal tissues, casein and the like including peptone broth, tryptic soy broth, nutrient broth, thioglycolate broth, and brain-heart infusion broth. Such protein hydrosylates contain many of the foregoing nutrients as well as providing numerous essential vitamins.

These basic broths may be fortified, if desired, with additional substrates such as glucose, dextrose and/or glycine. The composition of the growth medium may influence the metabolic activity of a microorganism. For example, a culture of *Proteus mirabilis* in unfortified tryptic soy broth exhibits primarily oxidative metabolism, consuming oxygen with little generation of gaseous by-products. A test of such a culture is a sealed vial resulted in a significant decrease in the pressure of the gas in the head space of the vial after four and one-half hours incubation. As no increase in the vial gas pressure occurred, any attempt at bacterial detection by monitoring for a pressure increase would have produced a false negative indication. But, when an identical culture of *Proteus mirabilis* was incubated in dextrose fortified tryptic soy broth, the organism exhibited primarily fermentative metabolism, first consuming oxygen and then generating large amounts of carbon dioxide. A test of the fortified culture showed a significant decrease in the vial gas pressure after between three and three and one-half hours incubation followed by a substantial pressure increase after nearly seven hours had elapsed. Not only do these results illustrate the effect of the culture medium on the metabolic activity of an organism, but they underscore the effectiveness of the vacuum detection procedure of the present invention.

As noted previously, culture medium 2 fills only a portion of vial 1. The remainder of the vial is filled with an oxygen containing gas referred to herein as the culture gas. The culture gas may be any gas or mixture of gases which will support the growth of oxygen consuming bacteria. Under most circumstances, ordinary air provides an acceptable culture gas for aerobic organisms. Air is not the only possible culture gas, however; synthetic bottle gases may be used. Reference numeral 3 is utilized to designate the culture gas. Vial 1 with the medium and culture gas therein is sealed with a cap 4. In the illustrated embodiment, cap 4 comprises a self-sealing rubber septum which allows fluid materials to be injected into or removed from the vial through hollow needles. The sealed vials with culture medium and culture gas inside are sterilized in an autoclave to prevent disruption of tests by bacteria from sources other than the test material.

Glass vials ranging in size from about 20 to about 100 ml make suitable test containers. The amount of liquid culture medium in the container may range from about 1/5 to about 4/5 of the volume of the container. The smaller the head space or gas space in the container, the greater the sensitivity of the test because the consumption of a given amount of oxygen will produce a greater vacuum, so that a given threshold of detection will be reached more rapidly. Care should be taken that the head space is not so small that changes occur in the composition of the culture gas which could adversely affect the growth of bacteria in the vial. The most preferred liquid volume is about ⅔ the volume of a standard 50 cc vial (total included volume approximately 65 cc).

Entering the container is a tube or needle 5 attached to a vacuum sensor 6. The sensor can be provided with an electrical output. This output can be of two kinds. It can be an analog output whose magnitude is proportional to the degree of vacuum produced in the vial. For example, a continuously operating linear analog pressure transducer could be used as the vacuum sensor. Alternatively, the sensor output can be a digital output whose magnitude changes suddenly and discontinuously whenever the vacuum in the vial exceeds a predetermined level. Such an output could be provided by using a vacuum operated diaphragm switch which actuates when a predetermined vacuum threshold is reached in the container as the vacuum sensor. The electrical output can be connected to commercially available amplifiers 7 and thence to appropriate visual display means 8, such as digitizers, recorders or printers, which display the signal in useable form to the operator. In addition, the electronics may contain a multiplexer or scanner 9 so that a plurality of test vials can be sequentially scanned at pre-selected time intervals, their vacuum levels sensed, and this information presented to the operator. Electrical sensors, either analog or digital, for low vacuum levels are readily available commercially. A suitable digital sensor (vacuum switch) is made by Dwyer Instruments, Inc., Michigan City, Ind. Suitable analog sensors (pressure transducers) may be obtained from the Robinson-Halpern Co., Plymouth Meeting, Pa. or from National Semiconductor Corp., Santa Clara, Calif. The pressure range required, normally ±50 cm $H_2O$ or approximately ±1 PSID, is well within the state-of-the-art of pressure measurement transducer technology. Suitable analog multiplexers are available commercially from Datel Systems, Inc., Canton, Mass., Burr-Brown, Tucson, Ariz., and from other suppliers.

A strictly mechanical sensor can be used in place of an electrical sensor. A mechanical sensor may be simpler, less expensive and more flexible, but it is otherwise equivalent to an electrical sensor. The advantages of the electrical sensor are that less operator attention is usually required, and that the vacuum changes can be recorded more readily for later study.

To initiate the testing of a material for the presence of bacteria, a sample of the material is introduced into a sterile vial containing culture medium and a quantity of oxygen containing gas. If the sample is a fluid, such as blood or urine, introduction of the sample can be effected by injecting it through septum 5 with a hypodermic needle. The method of the invention is particularly useful in medical testing of body fluids such as blood, lymph or urine. Care should be taken to sterilize the needle and the septum before making the injection in order to prevent contamination of the test vial. The septum, the sample injection needle and the vacuum sensor needle can be sterilized by wiping with 70% isopropanol and either burning off the alcohol in a flame or allowing it to evaporate. Solid materials may be tested by utilizing vials provided with apertures through the vial walls closed by tightly sealing, removable and replaceable caps.

After inoculation with the test material, the inoculated vial is incubated, i.e. subjected to conditions conducive to bacterial growth, for a predetermined period of time sufficient for growth of bacteria to consume some of the oxygen in the culture vial. It should be noted that the utility of the method of the invention is not limited to bacteria per se, and the term bacteria is intended to embrace other forms of oxygen consuming microbial life to which the invention is applicable. If photoresponsive or phototoxic microorganisms are of interest, light should be provided or excluded accordingly.

Since most medically significant bacteria achieve their maximum growth rates at temperatures of approximately 36° C. plus or minus 1° C., the culture vials are desirably maintained at a temperature lying in the range from about 35° C. to about 37° C. It is understood, however, that not all biologically active agents exhibit maximum growth within the recited temperature range. If it is of particular interest to determine whether or not a specific microorganism which grows better at some other temperature is present, then the temperature should be maintained at approximately that temperature at which the organism in question exhibits maximum growth.

Agitation of the culture medium also is useful both to produce growth of bacteria which may be present. A conventional shaking table may be utilized to effect gentle agitation. Alternatively, the culture medium can be stirred with a magnetic stirring bar magnetically coupled to a rotating magnet disposed beneath the culture vial.

During the incubation the vial is monitored, either continuously or periodically, for the production of a vacuum. A plurality of containers can be inoculated with test material samples and the containers repeatedly monitored seriatim at periodic time intervals throughout the time periods during which the containers and their contents are subjected to conditions conducive to bacterial growth. The length of the incubation period before testing for vacuum production and/or between subsequent tests depends on the particular application. Under favorably controlled conditions, the method of the invention is capable of detecting positive test results much more rapidly than conventional culturing techniques. Indeed, the speed of the method of the present invention compares favorably with the speed of radiometric assays utilizing radioactively labeled culture media.

In medical testing, positive test results may be observed after less than eight hours, in some cases within 2 to 4 hours after inoculation. Therefore in medical laboratories, continuous monitoring may be desirable. The rapidity of the method of the invention is of particular advantage in the medical field where prompt results can be a matter of life or death. If large numbers of samples are to be tested, it may be preferred to measure the pressure of the gas in each sample in succession after short intervals ranging from 10 minutes to one hour. Each test vial should be monitored either until positive results are observed or until it safely can be concluded that the sample is negative. A period of 24 to 48 hours without significant change in the pressure in the container is ordinarily sufficient to establish a negative sample.

After a short period of incubation, any oxygen consuming bacteria present in the sample will begin to grow in the culture medium thereby consuming nutrients from the medium and oxygen from the culture gas, and in many cases producing metabolic by-products. Gaseous by-products such as $CO_2$ or $H_2S$ may diffuse out of the culture medium into the culture gas thereby increasing the pressure of the gas in the vial and partially offsetting the vacuum produced by consumption of oxygen. Release of $CO_2$ from the culture medium into the culture gas may be substantially prevented if the pH of the medium is maintained above 6.5.

Since very small differences in gas pressure are being measured, and since the temperature affects the pressure of the gas directly and also indirectly by influencing the vapor pressure of the culture medium and the solubility gases in the medium, for maximum accuracy care should be taken to ensure that all vials in a given test are maintained at a constant temperature throughout the entire test. Commercially available incubators with temperature control to ±0.1° C. and uniformity to ±0.2° C. are considered satisfactorily precise under most circumstances. Desirably, the precision of the incubator system will be selected such that the maximum pressure deviation of the culture gas from thermal causes is less than 50% of the threshold of detection.

Alternatively, incubator systems with poorer temperature regulation might be used if temperature sensing means, such as a thermistor, were employed to monitor the incubator temperature, and the analog circuitry were programmed to correct the pressure reading for variations in incubation temperature.

For similar reasons, it is also desirable to warm the test vials to the temperature of the subsequent incubation prior to inoculating the test vials.

The production of a vacuum in the vial, at constant temperature, may be attributed to consumption of oxygen as a result of the metabolic activity of bacteria present in the test material.

The method of the invention requires a comparison of the gas pressure in an incubated test vial to a reference standard representing the initial pressure of the gas in order to detect the production of a vacuum due to the consumption of oxygen by bacteria in the medium. The reference standard may be developed either by direct measurement of the initial culture gas pressure immediately after inoculation of the test vial or by simultaneously measuring the gas pressure in an uninoculated, sterile control vial subjected to a parallel incubation treatment. The latter procedure has the advantage of compensating for thermal effects during the incubation period of allowing all measurements to be made at one time. The former procedure has the advantage of requiring only a single culture vial.

When a second vial is used as a reference vial, the pressures in the test vial and the reference vial are equilibrated after inoculation and prior to incubation of the test vial by venting them both to the atmosphere when air is used as the culture gas. A submicron filter interposed in the vent line prevents dust, airborne bacteria and other contaminants from entering the culture vial. Alternatively, equilibration of the pressure in the culture and reference vials may be effected by venting the vials to each other through a submicron filter to prevent contamination. The latter technique is useful when a culture gas other than air is being used in the vials.

An appeciable decrease in the pressure in an incubated vial compared to the initial gas pressure indicates the presence of bacteria in the test material. By an appreciable decrease is meant a difference greater than the ordinary maximum statistical deviation to be expected for the technique used to measure the pressure of the gas or attributable to minor variations in experimental conditions, e.g. vial temperature. Production of from 3 to 5 cm $H_2O$ vacuum in a 50 ml vial containing 25 to 30 ml of culture medium can be considered a positive indication of bacterial contamination.

The technique is simple to implement, since after incubation nothing is withdrawn from or admitted to the sample vial. It requires no radioactively labeled or otherwise exotic substrates, and lends itself favorably to automation.

Further details of the invention will be apparent from a consideration of the following tests:

Test I

Previously prepared and sterilized bottles containing 30 ml tryptic soy broth (TSB) without dextrose (27.5g/l) with stirring magnets included were each enriched with 0.4 ml of a sterile stock solution containing 1.5 g glycine in 20 ml deionized water. A 0.5 ml inoculum of a 4-day culture of *Pseudomonas pseudoalcaligenes* was used to inoculate one vial of glycine-enriched TSB. An uninoculated TSB vial was maintained with the TSB sample vial to serve as the pressure reference. The vials were placed in a stirrer-incubator at 37° C. for 40 minutes prior to inoculation. Pressure readings were taken at the time of inoculation and periodically thereafter as determined by the rate-of-change in the pressure with incubation time.

Figure 2:
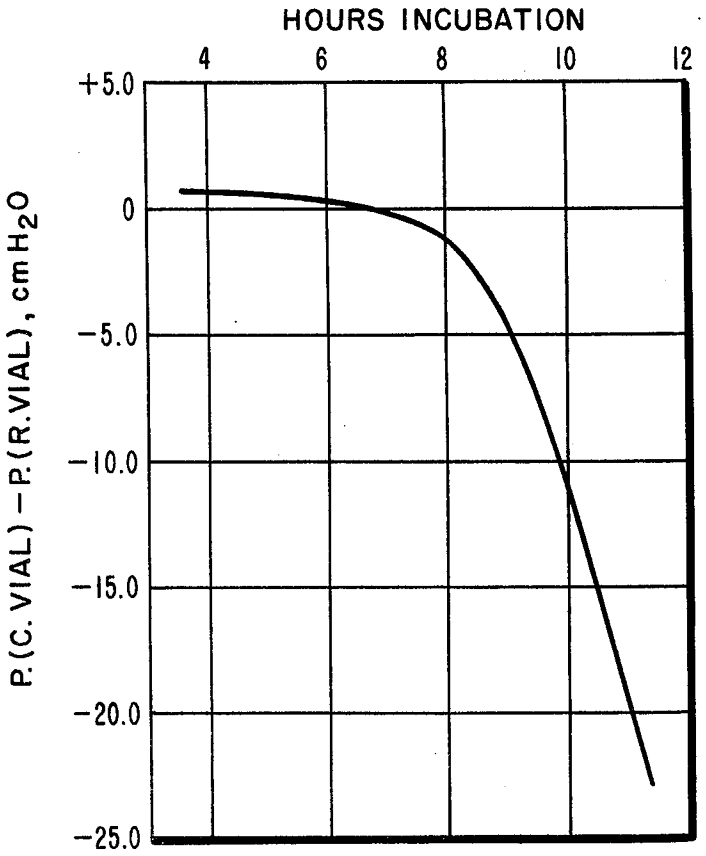
FIGS. 2 through 11 depict the results of tests demonstrating the effectiveness of the present invention.

Differential pressure measurements as a function of incubation time are presented graphically in FIG. 2. The oxidative nature of *Pseudomonas* metabolism is indicated by the extensive use of oxygen from the culture gas (air) as compared to any gas liberated by the organism. A pressure differential of minus 4 cm $H_2O$ in the test vial, considered to be a positive indication of bacterial growth, is reached after 9 hours incubaton.

A parallel radiometric assay utilizing a BACTEC®-bacteria detector manufactured by Johnston Laboratories, Inc., Cockeysville, Md. and a vial containing a $^{14}C$-labeled culture medium produced a positive test result between 10 and 11 hours after inoculation. The vacuum production measurement method of the present invention results in detection of microbial activity approximately 2 hours faster than the radiometric assay technique in this instance.

Test II

Two previously prepared and sterilized bottles containing 30 ml TSB were enriched with glycine as for Test I. A 0.5 ml inoculum of an overnight culture of *Pseudomonas aeruginosa* was used to inoculate one vial of glycine-enriched TSB. The uninoculated vial was maintained to serve as the pressure reference vial. The two vials were incubated and stirred for one hour at 36° C. prior to inoculation of the test vial. Pressure readings were obtained at the time of inoculation and periodically thereafter as determined by the pressure rate-of-change.

Figure 3:
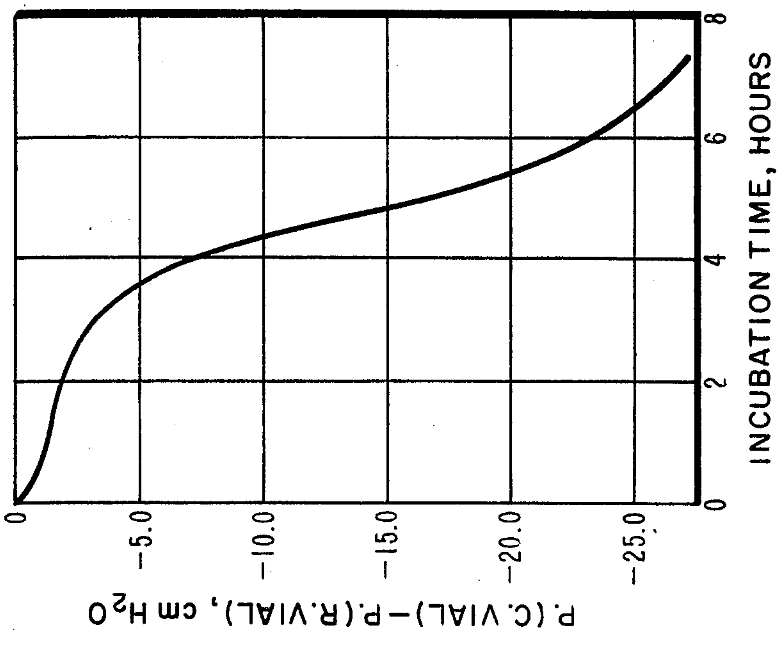

Differential pressure measurements as a function of incubation time are shown in FIG. 3. As in the case of *Pseudomonas pseudoalcaligenes,* far more oxygen is consumed from the culture gas than gas is produced by the organism. A positive growth indication of minus 4.0 cm $H_2O$ in the test vial was reached after 3¼ hours incubation. The results of a parallel radiometric determination indicate a positive determination after slightly less than 3 hours incubation time. Vacuum production by the organism produced detection within approximately ½ hour of the radiometric system in this instance.

Test III

Previously prepared and sterilized bottles with stirring magnets containing 30 ml enriched TSB medium having the following constituents and concentrations in deionized water were used for the *Streptococcus bovis* investigation: 27.5 g/l TSB without Dextrose, 2.5 g/l Dextrose Monohydrate, 1.0 g/l Glycine, 2.4 g/l Fructose and 0.4 g/l Sodium Bicarbonate. A 0.5 ml inoculum of an overnight culture of *Streptococcus bovis* was added by syringe to one vial of the enriched TSB medium. An uninoculated control vial of the TSB medium was maintained to serve as the pressure reference vial. The two vials were placed in a stirrer-incubator at 37° C. immediately following inoculation. Pressure readings were taken at the time of inoculation and periodically thereafter with a frequency dependent upon the pressure rate-of-change.

Figure 4:
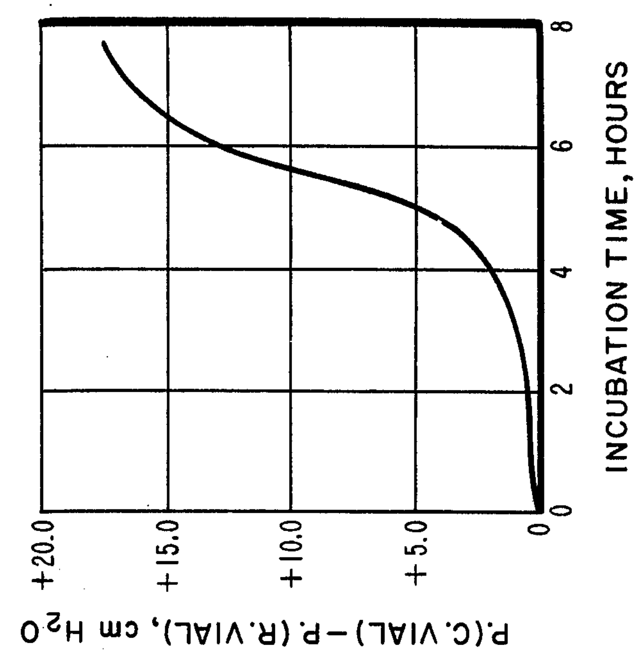

Results of the pressure measurements are plotted in FIG. 4. In contrast to the Pseudomonas study, this organism produces far more gas than it consumes from the head-space; no negative pressure differential is observed. Positive indication of bacterial growth by detection of a pressure increase (plus 4.0 cm $H_2O$) was noted after 5 hours incubation time. Positive detection of growth by a parallel radiometric assay was indicated after 3 hours incubation. The pressure measurement technique requires approximately two hours longer to detect *Streptococcus bovis.*

Test IV

Previously prepared and sterilized bottles with stirring magnets containing 30 ml TSB without dextrose (27.5 g/l) were each enriched with 0.4 ml of a sterile stock solution containing 4.0 g dextrose monohydrate in 20 ml deionized water. An overnight culture of *Escherichia coli* was used as the inoculum source with 0.2 cc of this culture being diluted in 30 ml TSB and 0.1 cc of the diluted culture being used to inoculate one TSB vial. An uninoculated vial was maintained to serve as the pressure reference vial. The vials were placed in a stirrer-incubator at 36° C. approximately one hour prior to inoculation. The differential culture gas pressure was read after venting at the time of inoculation and periodically thereafter as determined by organism growth.

Figure 5:
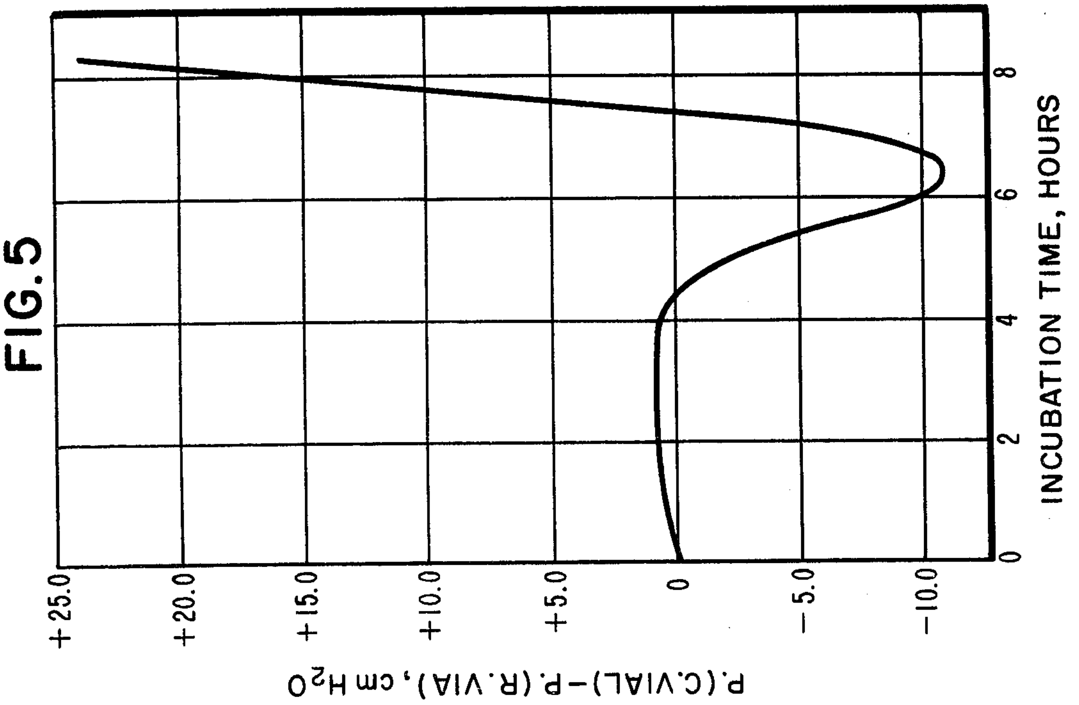

Pressure measurements results as a function of incubation time are presented in FIG. 5. Positive detection of microbial activity (minus 4.0 cm $H_2O$) by vacuum production occurs at 5¼ hours incubation time. A parallel radiometric assay resulted in positive detection after between 3 and 4 hours incubation.

The vacuum production measurement method of the present invention resulted in approximately one hour slower detection than the radiometric system in this instance. The shape of the pressure response curve strongly suggests that oxygen uptake by the organism precedes and exceeds gas production during the early stages of growth, permitting detection by measurement of vacuum production two hours prior to the production of any positive pressure.

Test V

Vials containing 30 ml enriched TSB prepared as for Test IV were used for this test. A 5-day culture of *Enterobacter cloacae* in Nutrient Broth was used as the source of inocula with 0.5 cc of this culture being diluted by addition to 30 ml enriched TSB and 0.2 ml of the diluted culture being used to inoculate one TSB vial. A pressure reference vial (TSB) was placed in the incubator-stirrer at 36.5° C. with the inoculated vial immediately following inoculation. Pressure measurements were begun after venting both vials at the time of inoculation to equalize pressures and repeated periodically thereafter. Readings were taken with increasing frequency as the pressure differential began to change rapidly.

Figure 6:
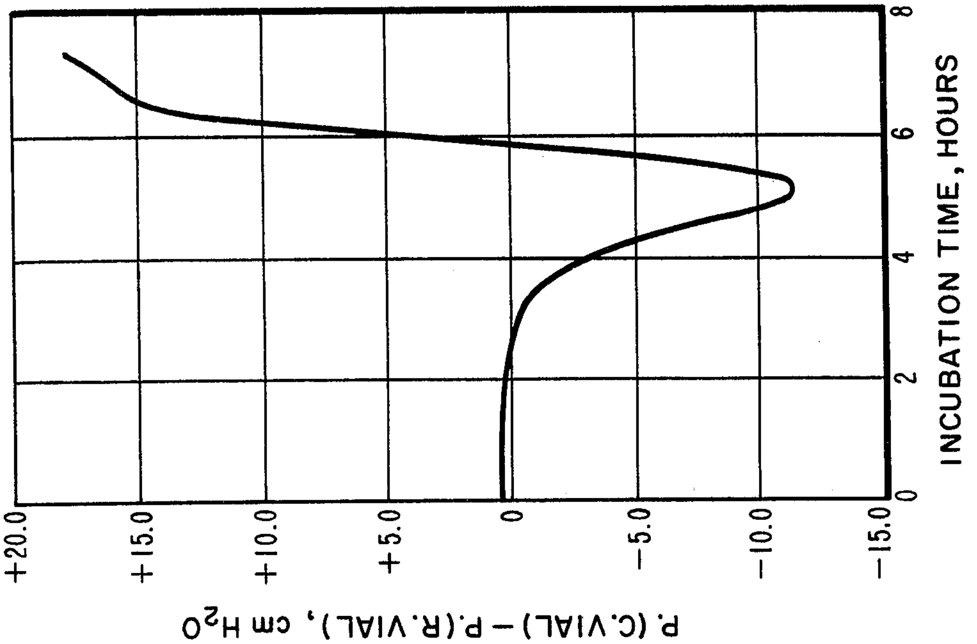

Results of the pressure measurements can be seen graphically in FIG. 6. Positive detection of bacterial growth (minus 4.0 cm $H_2O$) by vacuum production was obtained after 4¼ hours of incubation. A positive result from a parallel radiometric assay signifying detection, was obtained after slightly less than 3 hours incubation time.

Radiometric detection preceded vacuum detection of the growth of *Enterobacter cloacae* by approximately one hour. Significant vacuum production by the organism occured almost two hours earlier than production of any pressure greater than the initial pressure.

Test VI

Previously prepared and sterilized vials containing 30 ml TSB without dextrose were enriched with dextrose as per Test IV for use in this test. A fresh overnight culture of *Proteus mirabilis* was used as the source of inocula with 0.2 ml of this culture being diluted by addition to 30 ml TSB and 0.2 ml of the diluted culture being used to inoculate one enriched TSB vial. An uninoculated control vial was maintained to serve as the pressure reference vial.

Figure 7:
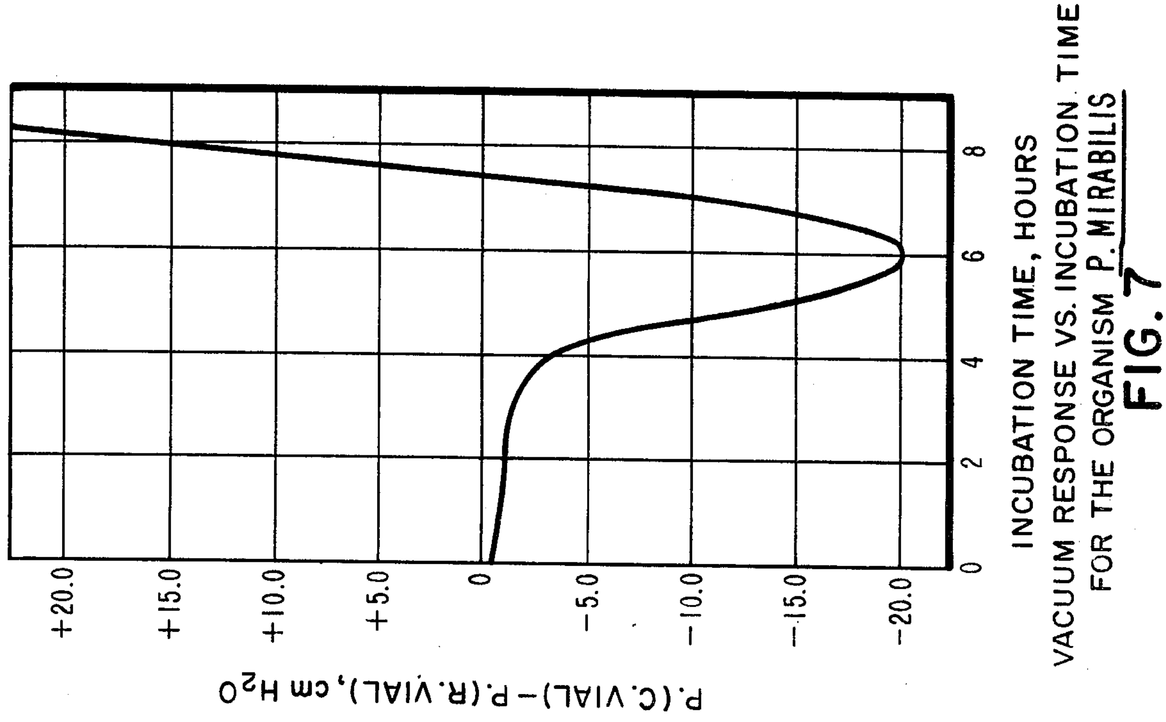

Results of the vacuum measurement are shown in FIG. 7. Vacuum production as a result of culture gas utilization gave a positive indication of growth after 4 hours incubation, fully three hours before any pressure greater than the initial pressure was produced. Growth indication by a parallel radiometric assay was evidenced after between 4 and 5 hours incubation time.

Detection of the growth of *Proteus mirabilis* was accomplished by both the vacuum method and the radiometric method after approximately the same incubation time. As with the other members of the Enterobacteriacae, vacuum production by the organism preceded the production of any pressure greater than the reference pressure.

Test VII

Two previously prepared and sterilized vials with stirring magnets containing 30 ml TSB without dextrose were enriched with dextrose monohydrate as in Test IV, and 0.1 ml of a fresh overnight culture of *Staphylococcus aureus* was used to inoculate one TSB vial. The uninoculated TSB vial was maintained as the pressure reference. The vials were incubated and stirred at 36° C.

for one hour prior to inoculation. Differential pressure measurements were taken after venting at the time of inoculation and periodically thereafter as determined by the pressure rate-of-change.

Figure 8:
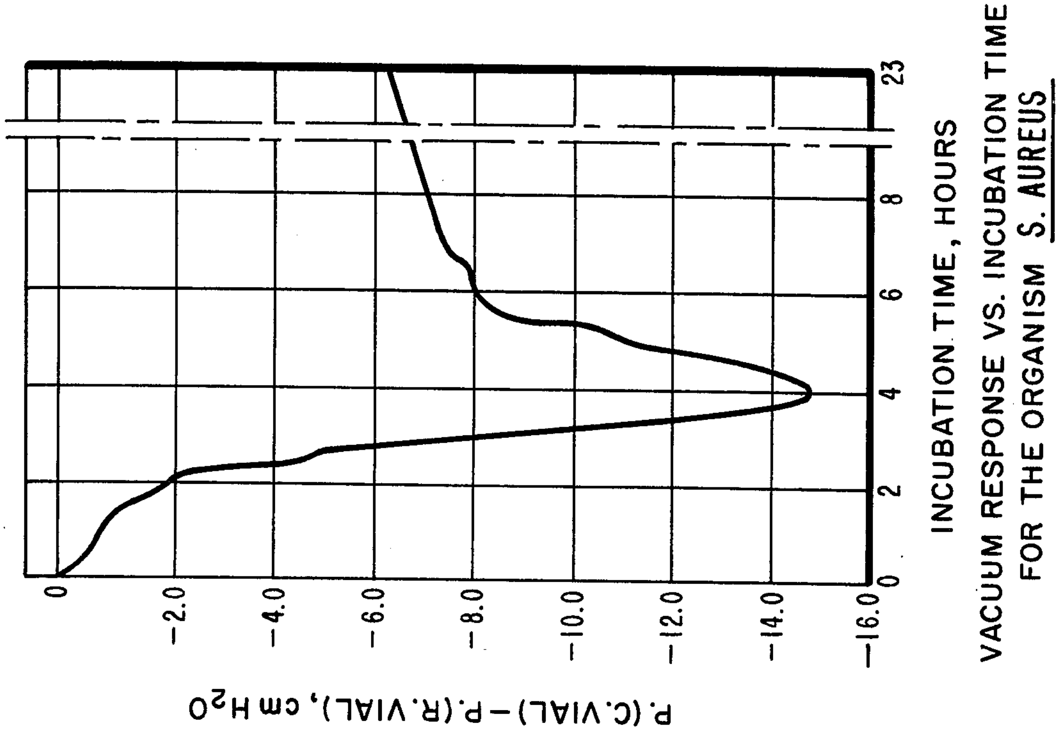

Results of the pressure measurements are presented in FIG. 8. Positive indication of microbial activity (minus 4.0 cm $H_2O$) was obtained by vacuum production after 2½ hours incubation time. Data from the parallel radiometric assay indicated positive growth detection after slightly less than 2 hours incubation.

Detection by pressure measurement lagged detection by the radiometric system by approximately ¾ hour for this organism. The shape of the pressure response curve suggests a relatively rapid uptake of oxygen from the culture gas, followed by a brief period during which gas production exceeds oxygen consumption of insufficient duration to permit the vial pressure to achieve a positive value. The result is a vacuum plateau about midway between zero pressure and the maximum vacuum value attained during the experiment. Significantly, no production of pressure greater than the reference pressure was noted. Any attempt to detect this organism by monitoring for an increase in vial pressure would result in an erroneous negative indication.

The measurement of microorganism vacuum production, although simple in concept and execution, is thus shown to be an effective tool for the determination of growth of various bacterial species.

It will be noted that there are significant differences in the shapes and forms of the vacuum and pressure curves shown in FIGS. 2 through 8 for the foregoing examples. The variety of pressure responses noted indicates that broad family or genus speciation may be possible on the basis of response curve shape and polarity. The enterobacteriacae (*E. cloacae, E. coli* and *P. mirabilis*) show a vacuum production followed by a rapid pressure rise. The pseudomonads (*P. aeruginosa* and *P. pseudoalcaligenes*) show a monotonic increase in vacuum with time with no positive pressure production. The staphlococcus (*S. aureus*) showed a net vacuum production made up of an initial higher vacuum component followed by a steady vacuum plateau. The nonfermenter *Strep. bovis* produced only a positive pressure. Thus, by recording the result of the monitoring step and comparing the recorded pattern of vacuum production to known patterns of vacuum production for known categories of microorganisms, it is possible to indicate broad family or genus speciation of bacteria on the basis of the shape of the observed response. This, together with a Gram stain of the culture, might assist the microbiologist in choosing appropriate selective media and biochemical tests for further identification of an unknown organism.

It has also been noted that the pattern of vacuum production by a bacterial culture with respect to time varies inversely with the number of bacteria present in the sample. In other words, the time required for a bacterial culture to produce a given threshold vacuum depends on the number of bacteria in the culture and decreases as the number of bacteria increases. This phenomenon may be utilized to determine the approximate number of bacteria present in an unknown sample. The following tests demonstrate the relationship between the number of bacteria in an inoculum and the rate of vacuum production, and illustrate the application of this principle to the determination of the number of bacteria in an unknown sample.

Test VIII

A fresh, overnight culture of *Escherichia coli* in dextrose-enriched tryptic soy broth was diluted as described in Test IV to obtain a base 100 inoculum. The base 100 inoculum was further diluted by adding 1 cc of it to 9 ml of culture medium to provide a base 10 inoculum. The base 10 inoculum was diluted still further by adding 1 cc of it to a second 9 ml portion of fresh culture medium to yield a base 1 inoculum. Six test vials each containing 30 ml dextrose-enriched tryptic soy broth culture medium, provided with magnetic stirring bars and caps with rubber septa were pre-incubated for one hour at 35.5° C., after which three of the vials were inoculated respectively with a 0.4 cc sample of the base 100 inoculum, the base 10 inoculum and the base 1 inoculum. The remaining three vials were used to provide a reference vial for each of the test vials. The pressure in each test vial was equalized with the pressure in its respective reference vial by venting the test vial and reference vial to each other thru a submicron filter to prevent contamination. Based on dilution of the original culture which had a microorganism concentration of approximately $10^9$ organisms per ml, the number of organisms in the base 100 vial was calculated to be approximately $8.7\times10^4$; the number in the base 10 vial to be approximately $8.7\times10^3$; and in the base 1 vial approximately $8.7\times10^2$. After inoculation, incubation of the vials was continued, and vacuum measurements were made on each of the vials periodically as determined by the rate of vacuum production versus incubation time. Measurements were made by connecting each test vial and its associated reference vial to opposite sides of a water manometer and noting the difference in the height of the water columns.

Figure 9:
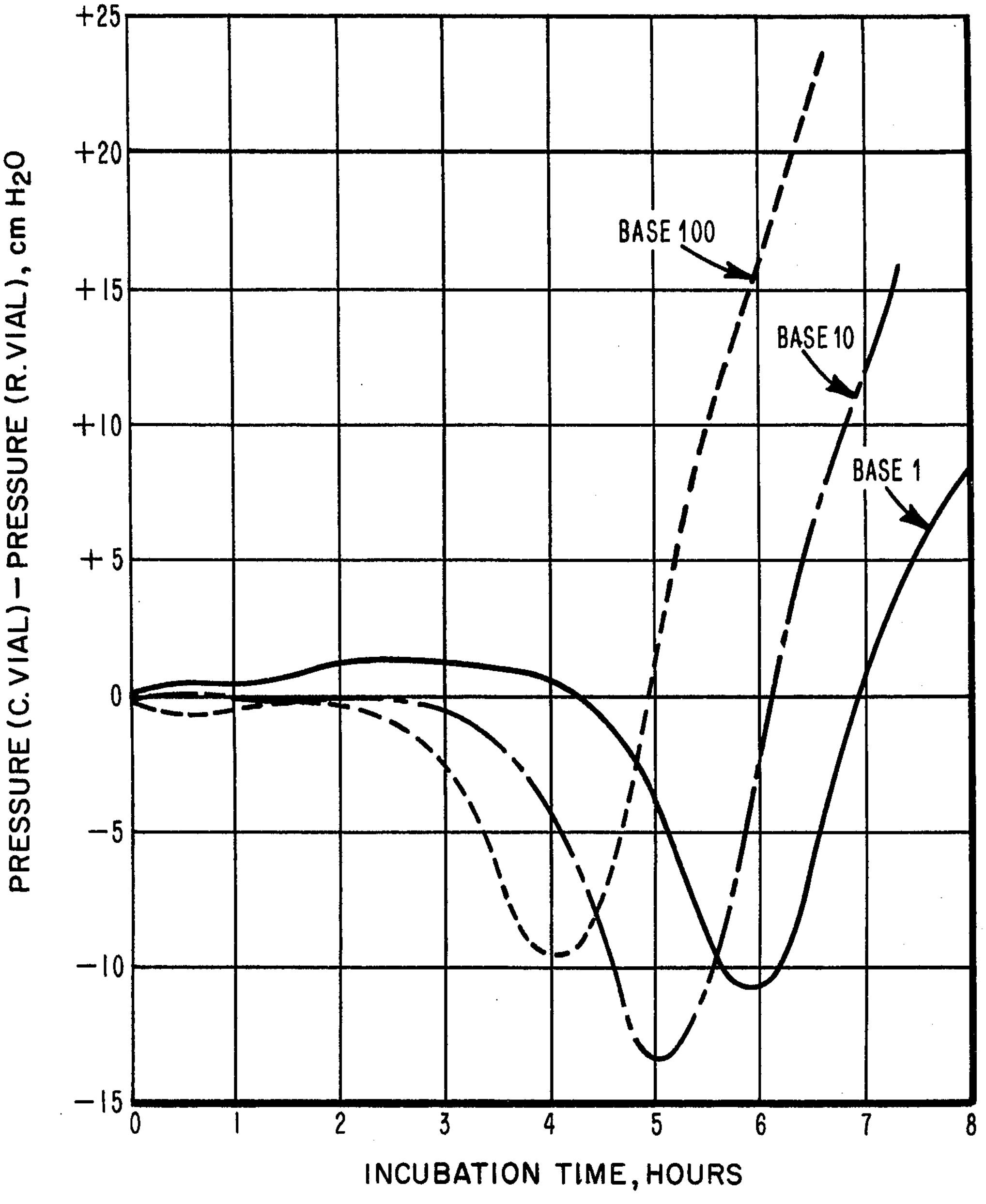
Figure 10:
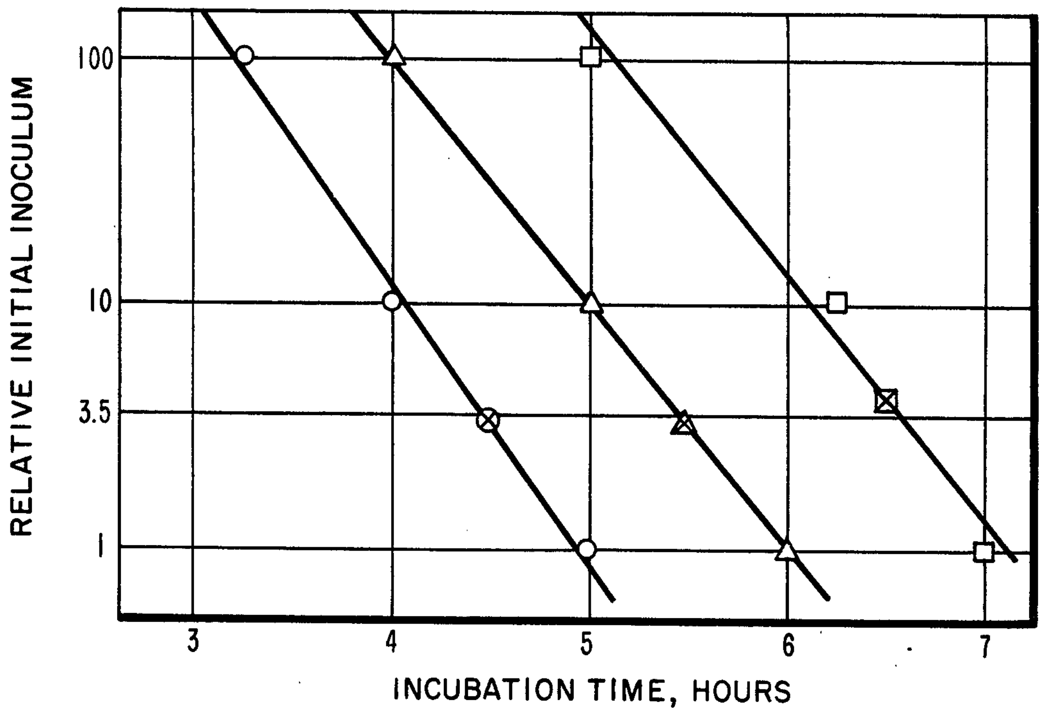

The results of the vacuum measurements are plotted in FIG. 9. The typical pattern of little initial pressure change followed by production of a vacuum and then by a substantial pressure increase was observed for all three samples. The time required for each sample to reach a 4 cm $H_2O$ threshold of detection, the time required to reach maximum vacuum production and the time required for each return to the initial pressure are listed in Table 1, and a semi-logarithmic plot of the initial number of bacteria in each sample versus these time values is shown in FIG. 10.

Table I

| *Escherichia coli* culture | Time to Reach Detection Threshold (hours) | Time to Reach Maximum Vacuum (hours) | Time to Regain Initial Pressure (hours) |
|---|---|---|---|
| Base 100 | 3¼ | 4 | 5 |
| Base 10 | 4 | 5 | 6½ |
| Base 1 | 5 | 6 | 7 |

It will be noted that the time required to reach each stage in the vacuum production pattern increases consistently as the number of microorganisms in the sample decreases.

Test IX

A culture vial identical to those used in Test VIII was inoculated with 0.4 ml of culture of *Escherichia coli* containing an unknown number of microorganisms and was incubated in the same manner as the vials in Test VIII while the production of vacuum in the vial was monitored. The threshold of bacterial detection (−4 cm $H_2O$) was reached after 4½ hours, maximum vacuum production occurred after approximately 5½ hours, and after approximately 6½ hours incubation, the pressure in the vial had returned substantially to its initial value. This pattern of response was compared to the patterns recorded for the samples containing known numbers of the same organism in Test VIII by plotting three points on FIG. 10 at the intersections of the three lines representing the time required to reach the vacuum threshold of detection, the time required to reach maximum vacuum and the time required to regain initial pressure and the time values observed for the unknown sample to reach the vacuum threshold of detection, maximum vacuum production and to regain initial pressure and by drawing a line generally through the points parallel to the x-axis of the graph and determining the ordinate value for the point at which the line intersects with y-axis of the graph. The product of the ordinate value at the point of intersection times the number of organisms in the base 1 inoculated test vial represents the approximate number of organisms in the unknown sample vial which in turn when divided by the volume of the inoculum introduced into the unknown sample vial yields a value for the number of organisms per unit volume in the unknown culture. The foregoing procedure results in a value of $7.5\times10^3$ *Escherichia coli* organisms per ml in the unknown culture.

Test X

Figure 11:
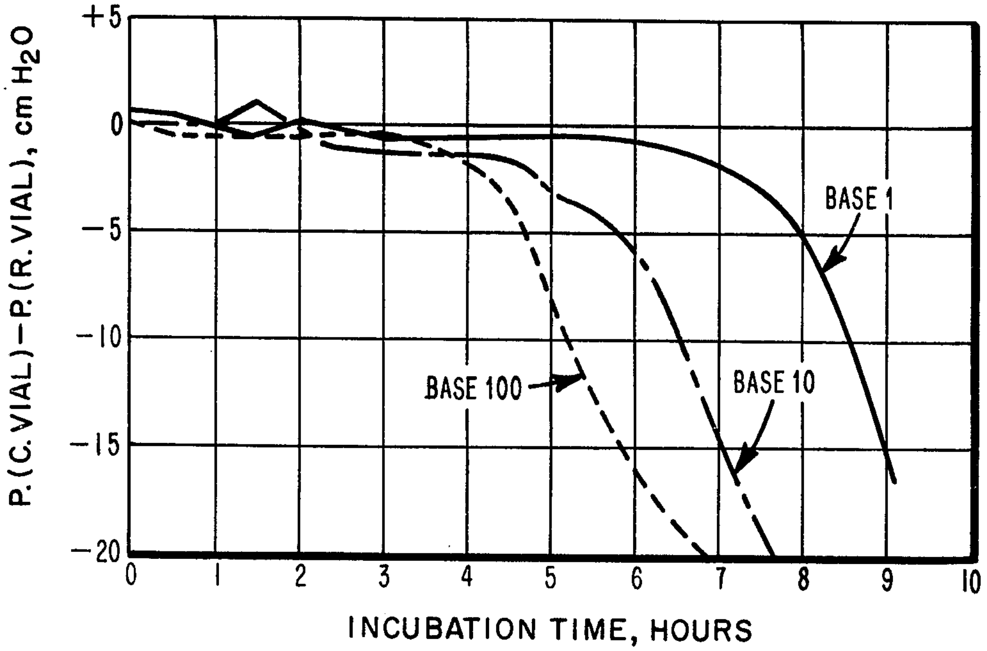

A two-week culture of *Pseudomonas aeruginsoa* was diluted by adding 1 cc of the culture to 30 ml of dextrose-enriched tryptic soy broth medium to provide a base 100 culture. The base 100 culture was diluted in turn by adding 1 cc of it to 9 ml dextrose-enriched tryptic soy broth medium to provide a base 10 culture which then was further diluted to provide a base 1 culture by mixing 1 cc of the base 10 culture with a second 9 ml portion of dextrose-enriched tryptic soy broth. A 0.4 cc inoculum of each of the three base cultures was injected into a separate test vial containing 30 ml of dextrose-enriched tryptic soy broth culture medium. Three uninoculated but otherwise identical vials were procured to provide a pressure reference vial for each sample vial. All six vials were incubated with stirring at 35.5° C. and vacuum readings were taken at the time of inoculation and periodically thereafter depending on the rate of vacuum production. The results of the vacuum measurements are shown in FIG. 11. The characteristic vacuum production pattern of an initial period of stability followed by a persistent increase in vacuum as previously noted in Tests I and II for *Pseudomonas* species is again apparent. The time required to reach the vacuum threshold of detection (−4 cm $H_2O$) for each of the three base cultures is tabulated in Table 2.

Table 2

| *Pseudomonas aeruginosa* Culture | Time to Reach Vacuum Detection Threshold (hours) |
|---|---|
| Base 100 | 4¾ |
| Base 10 | 5½ |
| Base 1 | 7¾ |

It can readily be seen that the response time varies inversely with the number of organisms in the initial inocula.

The foregoing embodiments have been described solely for purposes of exemplification and not by way of limitation. Since modifications of the disclosed embodiments may occur to persons skilled in the art, the scope of the invention is to be limited solely by the scope of the appended claims.

I claim:

1. A method of detecting oxygen consuming bacteria comprising the steps of:

(a) providing a sealable, sterile container containing a sterile, nonradioactive, liquid culture medium and a quantity of substantially hydrocarbon free, oxygen containing gas in the head space above said culture medium, (b) inoculating the container with a sample of material to be tested for the presence of oxygen consuming bacteria and sealing the container, (c) said container being connected to means for measuring reductions in the presence of the gas in said container, (d) establishing a reference standard representing the initial pressure of the gas in the container, (e) subjecting the sealed, inoculated container and its contents to conditions conducive to bacterial growth for a period of time sufficient for growth of bacteria to consume some of the oxygen, (f) retaining any gases evolved from the culture medium into the head space gas, in the head space gas, (g) measuring any reduction in the pressure of the gas in said container to a value less than said reference standard, and (h) comparing the measured pressure to said reference standard and determining whether there has occurred a reduction in pressure exceeding a predetermined threshold decrease indicating the presence of oxygen consuming bacteria; said threshold decrease being greater than any reduction attributable to measurement deviations or variations in experimental conditions.

2. A method as recited in claim 1 wherein said means for measuring reductions in the pressure of the gas is a continuously operating analog pressure transducer connected to recording means.

3. A method as recited in claim 1 wherein the material to be tested for the presence of bacteria is a liquid, said container being provided with a self-sealing rubber septum, and inoculation of the culture medium is effected by injecting a sample of said liquid test material into said container through said septum with a hypodermic syringe.

4. A method as recited in claim 1 wherein said culture medium comprises tryptic soy broth fortified with a material selected from the class consisting of glucose, dextrose and glycine.

5. A method as recited in claim 1 wherein said gas in said test container is air.

6. A method as recited in claim 1 wherein the volume of said test container is from about 20 to about 100 ml and the volume of said culture medium in said container is from about 1/5 to about 4/5 of the volume of said container.

7. A method as recited in claim 1 wherein said means for measuring reductions in the pressure of the gas comprises a vacuum operated switch which actuates an indicator system when a predetermined threshold decrease is reached in the container.

8. A method as recited in claim 7 wherein said predetermined threshold decrease detection level is from about 3 to about 5 cm $H_2O$.

9. A method as recited in claim 1 wherein a plurality of said containers are inoculated with test material samples and said containers are repeatedly monitored seriatim at intervals throughout the time periods during which the containers and their contents are subjected to conditions conductive to bacterial growth.

10. A method as recited in claim 9 wherein said periodic time intervals range from about 10 minutes to about 1 hour.

11. A method as recited in claim 1 wherein said culture medium in said container is agitated during the period of time the container and its contents are subjected to conditions conductive to bacterial growth.

12. A method as recited in claim 11 wherein said agitation is effected by gently shaking said container.

13. A method as recited in claim 11 wherein said agitation is effected by a magnetic stirring bar in said container, said stirring bar being subjected to the field of a rotating magnet outside said container.

14. A method as recited in claim 1 wherein said container and its contents are maintained at temperatures lying in the range between about 35° and about 37° C.

15. A method as recited in claim 14 wherein said container and its contents are maintained at a constant temperature.

16. A method as recited in claim 14 wherein the temperature of said container and its contents is brought to within the range from about 35° to about 37° C. prior to inoculation of the test container.

17. A method as recited in claim 1 wherein the references standard is established by providing an identical second sterile container containing culture medium and gas, maintaining the sterility of said container, subjecting said sterile container to the same conditions to which the inoculated container is subjected, monitoring the sterile container for the production of a vacuum.

18. A method as recited in claim 17 wherein the temperature of said test container and the temperature of said reference container are brought to within the range from about 35° to about 37° C. prior to inoculating said test container.

19. A method as recited in claim 17 wherein the initial pressure in said inoculated container and the initial pressure in said reference container are equilibrated prior to subjecting the containers to conditions conductive to bacterial growth.

20. A method as recited in claim 19 wherein the equilibration of pressures in said containers is effected by venting both containers to the atmosphere.

21. A method as recited in claim 1 wherein the pH of said culture medium is buffered to a pH between about 6 and about 8.

22. A method as recited in claim 21 wherein the pH of said culture medium is buffered to a pH between about 6.9 and 7.4.

23. In the identification of unknown microorganisms, the steps of, providing a sealable sterile container containing a sterile culture medium and a quantity of oxygen containing gas in the head space above said medium, inoculating said culture medium in said container with a sample of the organism to be identified and sealing the container, said container being connected to means for sensing the production of a vacuum in said container, subjecting the sealed, inoculated container to conditions conducive to bacterial growth for a period of time sufficient for growth of bacteria to consume some of the oxygen from the oxygen containing gas in said container, retaining in the head space gas any gases evolved from the culture medium into the head space gas, monitoring said container for the production of a vacuum due to consumption of oxygen, recording the result of the monitoring step and comparing the recorded pattern of vacuum production to known patterns of vacuum production for known categories of microorganisms.

24. In a method for detecting bacteria by providing a sealable sterile container containing a culture medium and a quantity of gas in the head space of said container above said culture medium, inoculating said culture medium in said container with a sample of material to be tested for the presence of bacteria and sealing the container, said container being connected to means for sensing the pressure of the gas within said container, subjecting the container and its contents to conditions conducive to bacterial growth for a predetermined period of time and monitoring the container during subjection to conditions conducive to bacterial growth for increases in the pressure of the gas within the container, the improvement comprising said container being connected to means for measuring reductions in the pressure of the gas in said container, said gas in said container comprising oxygen and being substantially free of hydrocarbon, establishing a reference standard representing the initial pressure of the gas in the container, retaining in said head space gas any gases evolved from the culture medium into the head space gas, measuring any reduction in the pressure of the gas in said container to a valve less than said reference standard, comprising the measured pressure to said reference standard and determining whether there has occurred a reduction in pressure exceeding a predetermined threshold decrease indicating the presence of oxygen consuming bacteria; said threshold decrease being greater than any reduction attributable to measurement deviations or variations in experimental conditions.

25. A method as recited in claim 19 wherein the equilibration of pressure in said containers is effected by venting the containers to each other through a submicron filter.

26. A method of determining the number of oxygen consuming bacteria present in a sample of material comprising the steps of:

(a) providing a sealable, sterile container containing a sterile, nonradioactive, liquid culture medium and a quantity of substantially hydrocarbon free, oxygen containing gas in the head space above said culture medium, (b) inoculating the container with a sample of material in which the number of oxygen consuming bacteria is to be determined and sealing the container, (c) said container being connected to means for sensing the production of a vacuum in said container, (d) subjecting the sealed, inoculated container and its contents to conditions conductive to bacterial growth for a period of time sufficient for growth of bacteria to consume some of the oxygen, (e) retaining any gases evolved from the culture medium into the head space gas, in the head space gas, (f) monitoring the pattern of vacuum production in said container with respect to time due to consumption of oxygen by bacteria growing in the liquid culture medium, and (g) comparing the monitored pattern of vacuum production from step (f) with the pattern of vacuum production for samples of material containing known numbers of the same bacteria treated in the same manner.

27. A method as recited in claim 26 wherein the pattern of vacuum production for a sample containing known numbers of the same bacteria is determined by parallel treatment of an identical culture medium containing vial inoculated with a known number of the same bacteria.

28. A method as recited in claim 26 wherein said container and its contents are maintained at temperatures lying in the range between about 35° and about 37° C.

29. A method as recited in claim 26 wherein said gas in said test container is air.

30. A method as recited in claim 26 wherein said vacuum sensing means is a continuously operating analog pressure transducer connected to recording means.

31. A method as recited in claim 26 wherein said culture medium in said container is agitated during the period of time the container and its contents are subjected to conditions conducive to bacterial growth.

32. A method as recited in claim 26 wherein the pH of said culture medium is buffered to a pH between about 6.9 and about 7.4.

33. A method according to claim 1 further comprising generating an output signal indicating when a reduction in pressure exceeding said threshold decrease has occurred.

34. A method according to claim 1 wherein said material to be tested for the presence of bacteria is a body fluid.

35. A method according to claim 34 wherein said body fluid is urine.

* * * * *